United States Patent [19]

Howe

[11] 4,135,910

[45] Jan. 23, 1979

[54] OXADIAZOL-3-YL-BENZOATES AS PLANT GROWTH REGULANTS

[75] Inventor: Robert K. Howe, Bridgeton, Mo.

[73] Assignee: Monsanto Company, St. Louis, Mo.

[21] Appl. No.: 796,249

[22] Filed: May 12, 1977

[51] Int. Cl.$^2$ .............................................. A01N 9/22
[52] U.S. Cl. ........................................... 71/92; 71/74; 71/76; 260/307 G; 560/35; 562/440
[58] Field of Search ................. 260/307 G; 71/76, 92, 71/74

[56] References Cited

U.S. PATENT DOCUMENTS

| | | | |
|---|---|---|---|
| 3,192,103 | 6/1965 | Sousa et al. | 167/33 |
| 3,211,742 | 10/1965 | Lenaers | 260/307 |
| 3,218,331 | 11/1965 | Eloy | 260/307 |
| 3,471,509 | 10/1969 | McKillip | 260/307 |
| 3,772,284 | 11/1973 | Singh et al. | 260/239 A |
| 3,882,138 | 5/1975 | Brouwer et al. | 260/307 G |
| 3,947,263 | 3/1976 | Brouwer et al. | 71/76 |
| 3,987,179 | 10/1976 | Nadelson | 424/272 |
| 4,016,170 | 4/1977 | Nadelson | 260/307 G |
| 4,032,644 | 6/1977 | Nadelson | 424/272 |

FOREIGN PATENT DOCUMENTS 837454 7/1976 Belgium.
2426878 1976 Fed. Rep. of Germany.

OTHER PUBLICATIONS

Katlkar-Phytochemistry 15, 1421-1424 (1976).
Harsonyi et al-C.A.68, 95829t (1968).
Brown et al.-Pesticide Science 4, 473-484 (1973).

*Primary Examiner*—Raymond V. Rush
*Attorney, Agent, or Firm*—Richard H. Shear; Donald W. Peterson

[57] ABSTRACT

Certain 2-[5-(aryl or substituted aryl)-1,2,4-oxadiazol-3-yl] benzoic acids, salts and esters having the formula:

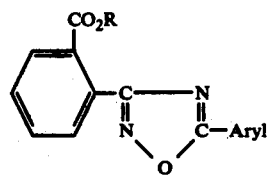

where R is hydrogen, lower alkyl and agriculturally acceptable cations and aryl is phenyl, naphthyl and phenyl substituted by one or more halogen, trifluoromethyl, lower alkyl or lower alkoxy moieties, (e.g., methyl 2-[5-(3-trifluoromethylphenyl)-1,2,4-oxadiazol-3-yl] benzoate), in a method of controlling undesirable vegetation and a method of regulating the growth of desirable plants.

1 Claim, No Drawings

OXADIAZOL-3-YL-BENZOATES AS PLANT GROWTH REGULANTS

The invention relates to novel oxadiazol-3-yl-benzoates as well as their use as agricultural chemicals. The novel compounds have been found to be effective in controlling the growth of undesired vegetation. At lower rates, the compounds have been found to be effective in regulating the growth of desirable plants.

The compounds of the invention may be represented by the following chemical formula

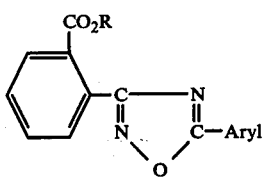

wherein R is selected from the group consisting of hydrogen, lower alkyl and agriculturally acceptable cations.

The term "Aryl" as used herein is understood to include pyridyl.

The oxadiazol-3-yl-benzoates of the invention may be prepared by reacting the appropriate ester of benzohydroxamoyl chloride with an appropriate benzonitrile. Benzohydroxamoyl chloride may be prepared in accordance with the following reaction scheme:

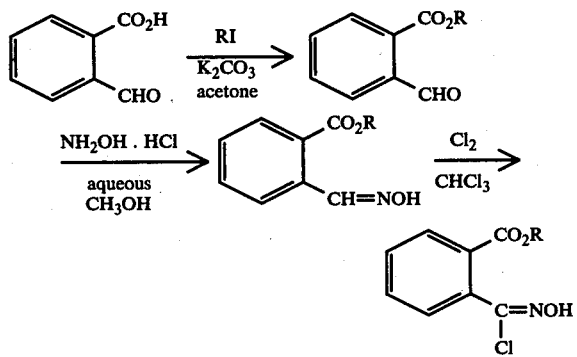

As is apparent to those skilled in the art, o-formylbenzoates may be prepared by known techniques. Addition of hydroxylamine hydrochloride in aqueous methanol results in 2-(hydroxyiminomethyl)benzoates which can be converted to the appropriate esters of benzohydroxamoyl chloride by the addition of chlorine in chloroform.

The following examples are presented to illustrate the preparation of the novel oxadiazol-3-yl-benzoates.

EXAMPLE 1

Preparation of o-Methoxycarbonylbenzohydroxamoyl Chloride. Methyl o-formylbenzoate was prepared in 81% yield from 2-carboxybenzaldehyde by the procedure of Brown and Sargent, Journal Chemical Society, P 1818 (1969). A solution of 1.64 g (0.010 mol) of methyl o-formylbenzoate and 1.05 g (0.015 mol) of hydroxylamine hydrochloride in 95 ml of 30% aqueous methanol was stirred at 23° C. for 50 minutes and then was cooled in ice. Scratching induced crystallization of 0.70 g of white solid (mp 73°–74.5° C.) which was methyl 2-(hydroxyiminomethyl) benzoate. Chlorine gas was slowly bubbled into a solution of 7.87 g (0.0439 mol) of methyl 2-(hydroxyiminomethyl)benzoate in 250 ml of $CHCl_3$ stirred at 0° C. (ice-methanol bath). A blue color formed, and the clear solution became cloudy. Within a few minutes, the blue reaction mixture turned green. After about 20 minutes, excess chlorine gas began to come through the solution, so chlorine addition was stopped and the solution was stirred in an ice bath for 1 hour until the green color had nearly all faded. Nitrogen gas was bubbled through the solution as it was allowed to warm to 20° C. during 30 minutes. The solution was concentrated under aspirator vacuum at 30°–40° C. The residue was triturated with 50 ml of ether, and the supernatant was decanted from a little insoluble gum and was concentrated to 7.21 g of viscous oil. This compound was identified as o-methoxycarbonylbenzohydroxamoyl chloride.

EXAMPLE 2

Preparation of Methyl 2-[5-(4-Chlorophenyl)-1,2,4-Oxadiazol-3-yl]Benzoate. To a solution of 10.0 g (0.0468 mol) of o-methoxycarbonylbenzohydroxamoyl chloride prepared in accordance with the above example and 71.8 g (0.522 mol) of purified p-chlorobenzonitrile in 400 ml of ether at 15°–20° C. was added dropwise with stirring a solution of 5.05 g (0.050 mol) of triethylamine in 25 ml of ether during 1.2 hours. The mixture was stirred at 23° C. for 27 hours, washed three times with water, and concentrated under vacuum to 130° C. at 30 torr. The 10.9 g of residue was chromatographed on 325 g of silica gel (Woelm, for dry column chromatography) with a 60:40 mixture of benzene and methylcyclohexane to give 3.81 g of product. This material was subjected to Kugelrohr distillation; after a small forerun at 100° C. (0.05 torr), 2.60 g of white solid was collected at 160° C. (0.1 torr). Recrystallization of the solid from methanol gave 2.40 g of solid, mp 102°–104° C.

Anal. Calc'd. for $C_{16}H_{11}ClN_2O_3$: C, 61.06; H, 3.52; N, 8.90. Found: C, 61.22; H, 3.40; N, 9.01.

EXAMPLE 3

Preparation of Methyl 2-[5-(4-Methoxyphenyl)-1,2,4-Oxadiazol-3-yl]Benzoate. To a solution of 10.0 g (0.0468 mol) of o-methoxycarbonylbenzohydroxamoyl chloride and 67 g (0.50 mol) of p-anisonitrile in 300 ml of ether was added, with stirring at 20°–25° C., a solution of 5.05 g (0.050 mol) of triethylamine in 15 ml of ether during 1 hour. The reaction mixture was stirred at 20°–25° C. for 20 days, washed three times with water, dried ($CaSO_4$), and concentrated under vacuum. The residue was subjected to Kugelrohr distillation. The excess p-anisonitrile was collected at 100° C. (1.8 torr). The product was collected in the next fraction at 140°–190° C. (0.15 torr). This material was redistilled; after a forerun taken at 140°–160° C. (0.05 torr), 97% pure product, 5.48 g (38%), was collected at 175°–180° C. (0.1 torr) as a viscous oil. Two crystallizations of the oil from methanol gave 2.80 g of pure product as a white solid, mp 73°–75° C.

Anal. Calc'd. for $C_{17}H_{14}N_2O_4$: C, 65.80; H, 4.55; N, 9.03. Found: C, 65.56; H, 4.48; N, 8.97.

EXAMPLE 4

Preparation of Methyl 2-[5-(3-Trifluoromethylphenyl)-1,2,4-Oxadiazol-3-yl]Benzoate. To a solution of 8.0 g (0.0374 mol) of o-methoxycarbonylbenzohydroxamoyl chloride and 64 g (0.374 mol) of m-trifluoromethylbenzonitrile in 150 ml of ether was added, with stirring at 20°–25° C., a solution of 4.0 g (0.0396 mol) of triethylamine in 15 ml of ether during 1 hour. The reaction mixture was stirred at 20°–25° C. for 10 days, washed three times with water, dried (CaSO$_4$), and concentrated under vacuum to 63.5 g of residue. This material was subjected to Kugelrohr distillation; excess nitrile was removed at 80°–90° C. (8 torr). After a small fraction collected up to 150° C. at 0.1 torr, about 98% pure product was collected at 150° C. (0.15 torr) as an oil. This oil was crystallized from methanol to give 4.88 g (37%) of white solid, mp 84.5°–86.5° C.

Anal. Calc'd. for C$_{17}$H$_{11}$F$_3$N$_2$O$_3$: C, 58.63; H, 3.18; N, 8.04. Found: C, 58.63; H, 3.16; N, 7.96.

Similarly, the following compounds have been prepared.

EXAMPLE 5

Methyl 2-[5-(2-Pyridyl)-1,2,4-Oxadiazol-3-yl]Benzoate.

Anal. Calc'd.: C, 64.05; H, 3.94; Found: C, 64.06; H, 3.95.

EXAMPLE 6

Methyl 2-[5-Phenyl-1,2,4-Oxadiazol-3-yl]Benzoate.
Anal. Calc'd.: C, 68.56; H, 4.32; H, 9.99; Found: C, 68.47; H, 4.38; N, 10.04.

EXAMPLE 7

Methyl 2-[5-(1-Naphthyl)-1,2,4-Oxadiazol-3-yl]Benzoate.
Anal. Calc'd.: C, 72.72; H, 4.27; Found: C, 72.48; H, 4.33.

Acids may be prepared by hydrolysis of the appropriate ester. Salts may be prepared by reaction of the free acid with the appropriate base.

Preferred are those oxadiazol-3-yl-benzoates in which the Aryl is phenyl or phenyl substituted by one or more halogen, trifluoromethyl, lower alkyl or lower alkoxy moieties.

As used herein, the term "lower alkyl" or "lower alkoxy" is understood to mean those alkyl or alkoxy groups having from 1 to 5 carbon atoms, inclusive.

The term "agriculturally acceptable cations" is understood to mean those cations which are commonly used in agricultural compositions to form the salt of the free acid, including but not limited to the alkali metal, substituted amine and ammonium cations.

As noted above, the compounds of the present invention have been found to be effective in the partial or total inhibition of undesirable vegetation. Table I summarizes results of tests conducted to determine the pre-emergent as well as the post-emergent herbicidal activity of the compounds.

The pre-emergent test was conducted as follows:

A good grade of top soil was placed in aluminum pans and compacted to a depth of three-eighths to one-half inch from the top of the pan. On the top of the soil was placed a predetermined number of seeds or vegetative propagules of various plant species. The soil required to level fill the pans after seeding or adding vegetative propagules was weighed into a pan. A known amount of the active ingredient applied in a solvent or as a wettable powder and the soil were thoroughly mixed, and used as a cover layer for prepared pans. After treatment, the pans were moved into a greenhouse bench where they were watered from below as needed to give adequate moisture for germination and growth.

Unless noted otherwise, approximately 4 weeks after seeding and treating, the plants were observed and the results recorded. The herbicidal rating was obtained by means of a fixed scale based on the average percent injury of each seed lot. The ratings are defined as follows:

| % Control | Rating |
|---|---|
| 0-24 | 0 |
| 25-49 | 1 |
| 50-74 | 2 |
| 75-100 | 3 |

The post-emergent tests were conducted as follows:

The active ingredients are applied in spray form to two or three-week old specimens of various plant species. The spray, a solution or wettable powder suspension containing the appropriate rate of active ingredient to give the desired test rate and a surfactant, is applied to the plants. The treated plants are placed in a greenhouse and unless otherwise noted approximately 4 weeks later the effects ranging from no response to total inhibition are observed and recorded. The results are shown in Table I in which the post-emergent herbicidal activity index is as follows:

| % Control | Rating |
|---|---|
| 0-24 | 0 |
| 25-49 | 1 |
| 50-74 | 2 |
| 75-99 | 3 |
| 100 | 4 |

The plant species utilized in these tests are identified by letter in accordance with the following legend:

A Soybean  I Hemp Sesbania
B Sugarbeet  J Lambsquarters
C Wheat  K Smartweed
D Rice  L Velvet Leaf
E Sorghum  M Bromus Tectorum
F Cocklebur  N Panicum Spp.
G Wild Buckwheat  O Barnyard Grass
H Morning Glory  P Crabgrass Table 1

| Compound | WAT* | kg h | Pre-Emergent Plant Species | | | | | | | | | | | | | | |
|---|---|---|---|---|---|---|---|---|---|---|---|---|---|---|---|---|---|
| | | | A | B | C | D | E | F | G | H | I | J | K | L | M | N | O | P |
| 2 | 2 | 1.12 | 0 | 0 | 0 | 1 | 0 | 0 | 0 | 0 | 0 | 1 | 0 | 1 | 0 | 0 | 0 | 1 |
| | 2 | 5.60 | 0 | 1 | 1 | 1 | 1 | 0 | 1 | 1 | 1 | 2 | 2 | 1 | 0 | 0 | 1 | 1 |
| 3 | 2 | 1.12 | 1 | 0 | 0 | 1 | 0 | 0 | 0 | 0 | 1 | 2 | 0 | 1 | 0 | 0 | 0 | 2 |
| | 4 | 5.60 | 2 | 2 | 0 | 2 | 1 | 0 | 0 | 1 | 3 | 2 | 1 | 1 | 0 | 0 | 2 | 2 |
| 4 | 4 | 1.12 | 1 | 1 | 1 | 2 | 2 | 0 | 1 | 1 | 2 | 2 | 1 | 1 | 2 | 2 | 3 | 2 |
| | 4 | 5.60 | 2 | 2 | 2 | 3 | 2 | 1 | 1 | 1 | 2 | 3 | 2 | 1 | 2 | 3 | 3 | 3 |
| 7 | 2 | 1.12 | 2 | 1 | 1 | 2 | 1 | 1 | 3 | 2 | 1 | 0 | 1 | 0 | 1 | 1 | 3 | 3 |

Table 1-continued

| 4 | 1.12 | 1 | 1 | 1 | 2 | 0 | 0 | 2 | 2 | 0 | 1 | 0 | 0 | 1 | 0 | 3 | 2 |
| 2 | 5.60 | 1 | 1 | 1 | 3 | 3 | 1 | 3 | 2 | 1 | 3 | 2 | 1 | 2 | 2 | 3 | 3 |
| 4 | 5.60 | 1 | 1 | 2 | 2 | 2 | 2 | 3 | 2 | 1 | 3 | 1 | 1 | 1 | 2 | 3 | 2 |

*Weeks after treatment

The compounds were also tested by utilizing the above procedure on the following plant species:

A Canada Thistle    G Nutsedge
B Cocklebur    H Quackgrass
C Velvet Leaf    I Johnson Grass
D Morning Glory    J Downy Brome
E Lambsquarters    K Barnyard Grass
F Smartweed The results are summarized by Table II.

Table II

| Compound | WAT* | kg h | Pre-Emergent Plant Species | | | | | | | | | | |
|---|---|---|---|---|---|---|---|---|---|---|---|---|---|
| | | | A | B | C | D | E | F | G | H | I | J | K |
| 2 | 2 | 11.2 | 0 | 0 | 0 | 0 | 0 | 0 | 0 | 0 | 0 | 0 | 0 |
|   | 4 | 11.2 | 2 | 0 | 1 | 0 | 1 | 2 | 0 | 2 | 0 | 0 | 1 |
| 3 | 4 | 11.2 | 3 | 0 | 1 | 0 | 3 | 1 | 0 | 2 | 0 | 1 | 1 |
| 4 | 4 | 11.2 | 3 | 1 | 1 | 2 | 3 | 2 | 2 | 3 | 2 | 3 | 3 |
| 5 | 4 | 11.2 | 1 | 0 | 0 | 0 | 1 | 0 | 0 | 0 | 0 | 0 | 0 |
| 6 | 4 | 11.2 | 2 | 0 | 1 | 1 | 2 | 2 | 0 | 1 | 0 | 1 | 1 |
| 7 | 4 | 11.2 | 2 | 0 | 1 | 2 | 3 | 1 | 2 | 1 | 0 | 2 | 3 |

| Compound | WAT* | kg h | Post-Emergent Plant Species | | | | | | | | | | |
|---|---|---|---|---|---|---|---|---|---|---|---|---|---|
| | | | A | B | C | D | E | F | G | H | I | J | K |
| 2 | 2 | 11.2 | 1 | 0 | 1 | 0 | 1 | 4 | 0 | 0 | 0 | 0 | 0 |
| 3 | 4 | 11.2 | 1 | 0 | 1 | 0 | 0 | 0 | 0 | 0 | 0 | 0 | 0 |
| 4 | 2 | 11.2 | 1 | 1 | 1 | 1 | 1 | 2 | 0 | 0 | 0 | 0 | 0 |
| 5 | 4 | 11.2 | 0 | 1 | 1 | 0 | 3 | 0 | 0 | 0 | 0 | 0 | 0 |
| 6 | 4 | 11.2 | 1 | 0 | 1 | 1 | 1 | 1 | 0 | 1 | 0 | 0 | 0 |
| 7 | 4 | 11.2 | 1 | 2 | 2 | 2 | 2 | 0 | 1 | 0 | 0 | 0 | 1 |

*Weeks after treatment

The above table illustrates one aspect of the present invention. That is, the use of the compounds of the invention to kill or injure undesirable plants, e.g. weeds. Another aspect of the invention, however, is the use of said compounds to regulate the growth of desirable plants especially dicotyledonous plants such as legumes.

As used herein, the regulation of "plant growth or development" is understood to mean the modification of the normal sequential development of a treated desirable plant to agricultural maturity. Such modifications are most readily observed as changes in size, shape, color or texture of the treated plant or any of its parts. Similarly, changes in the quantity of plant fruit or flowers are also quite apparent from visual inspection. The above changes may be characterized as an acceleration or retardation of plant growth, stature reduction, leaf or canopy alteration, increased branching, terminal inhibition, increased flowering, defoliation, increased root growth, increased cold hardiness and the like. While many of these modifications are desirable in and of themselves, most often it is their effect on the economic result that is of most importance. For example, a reduction in stature of the plant permits the growing of more plants per unit area. A darkening of the foliar color may be illustrative of higher chlorophyll activity indicative of improved rate of photosynthesis.

Although the regulation of plant growth in accordance with the present invention may include partial inhibition of plant growth, it does not include the total inhibition or killing of such plants. The present invention contemplates the use of an amount of active ingredient which will modify the normal sequential development of the treated plant to agricultural maturity. Such plant growth regulating amounts may vary, not only with the material selected, but also with the modifying effect desired, the species of plant and its stage of development, the plant growth medium and whether a permanent or a transitory effect is sought. It is, however, well within the skill of the art to determine the amount of active ingredient required.

Modification of the plants may be accomplished by applying the active ingredient to seeds, emerging seedlings, roots, stems, leaves, flowers, fruits or other plant parts. Such application may be made directly to the plant part, or indirectly by application to the plant growth medium. Foliar applications to plants beginning to blossom is preferred.

Utilizing Compounds 2 and 5 as the active ingredient in a plant growth regulating composition containing 266 ppm of said compound, said compounds were found to possess plant growth regulating activity when tested in accordance with the following procedure.

Soybean plants, variety Clark 63, were grown in a greenhouse or a growth chamber to the one-half expanded unifoliate state. At that time, the plants were treated by dipping the plants into an aqueous solution of the chemical, acetone and a surfactant. After growing the plants for approximately two weeks under cool conditions (11°-14° C.), the plants were transferred to a greenhouse and grown at 24° C. Approximately four weeks after treatment, the plants were observed and compared with control plants that had been dipped into water containing only the surfactant. Plants treated with Compound 2 were observed to have undergone a reduction in stature as well as development of axillary buds and an inhibition of leaf growth. Those treated with Compound 5 were observed to have undergone development of axillary buds, inhibition of leaf growth and epinasty.

Compounds 2, 3 and 4 were further tested as follows.

A number of soybean plants, variety Williams, are grown from seeds in plastic pots in the greenhouse for a period of one week at which time the plants are thinned to one plant per pot. When the second trifoliate leaf (three weeks) is fully expanded, the plants are treated with a solution of the active ingredient in acetone and water. Aqueous Tween 20 is used as a surfactant.

When the fifth trifoliate leaf (four to five weeks) is fully expanded, the treated plants are compared with the non-treated control plants and the observations recorded.

Table III below summarizes the results and observations made in accordance with the above procedure.

Table III

| Compound | kg/h | Observations |
| --- | --- | --- |
| 2 | 2.8 | Stature reduction, axillary bud development, stem distortion, leaf distortion, inhibition of apical development. |
|  | 0.56 | Stature reduction, axillary bud development, stem distortion, leaf alteration, altered canopy. |
|  | 0.11 | Leaf alteration. |
| 3 | 2.8 | Stature reduction, leaf alteration. |
|  | 0.56 | No response. |
|  | 0.11 | No response. |
| 4 | 2.8 | Stature reduction, stem distortion, leaf distortion, leaf alteration, altered canopy. |
|  | 0.56 | Stature reduction, stem distortion, leaf distortion, leaf alteration, altered canopy. |
|  | 0.11 | Leaf alteration. |

In selecting the appropriate rate of application of the active ingredient, it will be recognized that precise rates will also be dependent upon the desired response, mode of application, plant variety, soil conditions and various other factors known to those skilled in the art. While a rate of about 0.056 to 5.6 kilos per hectare is preferred, higher rates of up to 56 kilos per hectare may be used, depending upon the factors noted above. In addition, it will be recognized that single or multiple applications may be used to exert the desired response.

The above data illustrate that the compounds of the invention are effective herbicides especially at higher rates of application, e.g. above 1.12 kilograms per hectare. At lower rates, below 5.6 kilograms per hectare and preferably from 0.056 to about 3.36 kilograms per hectare, the compounds of the invention are effective in regulating the growth of leguminous plants, e.g. soybeans.

In the practice of the invention, the active ingredient can be used alone or in combination with a material referred to in the art as an adjuvant in either liquid or solid form. To prepare such compositions, the active ingredient is admixed with an adjuvant including diluents, extenders, carriers and conditioning agents to provide compositions in the form of finely-divided particulate solids, granules, pellets, wettable powders, dusts, solutions and aqueous dispersions or emulsions. Thus, the active ingredient can be used with an adjuvant such as a finely-divided particulate solid, a solvent liquid of organic origin, water, a wetting agent, dispersing agent or emulsifying agent or any suitable combination of these.

Illustrative finely-divided solid carriers and extenders which are useful in plant growth regulating compositions of this invention include the talcs, clays, pumice, silica, diatomaceous earth, quartz, Fullers earth, sulfur, powdered cork, powdered wood, walnut flour, chalk, tobacco dust, charcoal and the like. Typical liquid diluents include Stoddard solvent, acetone, alcohols, glycols, ethyl acetate, benzene and the like. The plant growth regulating compositions of this invention, particularly liquids and wettable powders, usually contain one or more surface-active agents in amounts sufficient to render a given composition readily dispersible in water or in oil. The term "surface-active agent" is understood to include wetting agents, dispersing agents, suspending agents and emulsifying agents. Such surface-active agents are well known and reference is made to U.S. Pat. No. 2,547,724, Columns 3 and 4, for detailed examples of the same.

Generally, the active ingredients are applied in the form of a composition containing one or more adjuvants which aid in the application of a uniform distribution of the active ingredient. The application of liquid and particulate solid compositions of the active ingredient can be carried out by conventional techniques utilizing, for example, spreaders, powder dusters, boom and hand sprayers and spray dusters. The composition can also be applied from airplanes as a dust or spray.

Compositions of this invention generally contain from about 1 to 99 parts active ingredient, about 1 to 50 parts surface-active agent and about 4 to 94 parts solvents, all parts being by weight based on the total weight of the composition.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A method of regulating the growth of desirable plants which comprises applying to said plants an effective amount of a compound having the formula

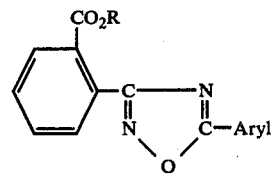

wherein R is selected from the group consisting of hydrogen, lower alkyl and agriculturally acceptable cations; Aryl is phenyl substituted by one trifluoromethyl.

* * * * *